US010444011B2

(12) United States Patent
Jingu

(10) Patent No.: US 10,444,011 B2
(45) Date of Patent: Oct. 15, 2019

(54) SAMPLE FOR COORDINATES CALIBRATION AND METHOD FOR FABRICATING THE SAME

(71) Applicant: Hitachi High-Technologies Corporation, Minato-ku, Tokyo (JP)

(72) Inventor: Takahiro Jingu, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 270 days.

(21) Appl. No.: 15/528,692

(22) PCT Filed: Nov. 25, 2014

(86) PCT No.: PCT/JP2014/081015
§ 371 (c)(1),
(2) Date: May 22, 2017

(87) PCT Pub. No.: WO2016/084124
PCT Pub. Date: Jun. 2, 2016

(65) Prior Publication Data
US 2017/0268870 A1 Sep. 21, 2017

(51) Int. Cl.
*G01B 21/04* (2006.01)
*G01N 21/956* (2006.01)
(Continued)

(52) U.S. Cl.
CPC .......... *G01B 21/042* (2013.01); *G01N 21/93* (2013.01); *G01N 21/956* (2013.01); *G03F 7/7065* (2013.01)

(58) Field of Classification Search
CPC .................................................... G01B 21/042
(Continued)

(56) References Cited

U.S. PATENT DOCUMENTS

| 6,535,781 | B1* | 3/2003 | Tsutsumi | ............... H01J 37/28 700/121 |
| 2007/0072091 | A1* | 3/2007 | Smith | ................ G03F 7/70458 430/5 |

(Continued)

FOREIGN PATENT DOCUMENTS

| JP | 11-64239 A | 3/1999 |
| JP | 2000-58606 A | 2/2000 |

(Continued)

OTHER PUBLICATIONS

International Search Report (PCT/ISA/210) issued in PCT Application No. PCT/JP2014/081015 dated Jan. 13, 2015 with English translation (four (4) pages).

(Continued)

*Primary Examiner* — Ricky Ngon
(74) *Attorney, Agent, or Firm* — Crowell & Moring LLP

(57) ABSTRACT

A sample for coordinates calibration including (1) a substrate having a circular plate-shape, and (2) multiple intentional defects that form a grid pattern with squares as unit grids on a surface of the substrate, the intentional defect providing a center point of the grid pattern coinciding with a center point of the substrate and, letting the maximum value of a number of the unit grids arranged from the center point of the substrate in radial directions be N (a natural number equal to or larger than two), a number of the intentional defects formed at equal spaces along one side of the unit grid being N+1 including the two intentional defects providing a vertex of the unit grid is proposed.

12 Claims, 6 Drawing Sheets

(51) Int. Cl.
  *G03F 7/20* (2006.01)
  *G01N 21/93* (2006.01)
(58) Field of Classification Search
  USPC .......................................................... 702/95
  See application file for complete search history.

(56) References Cited

U.S. PATENT DOCUMENTS

| | | | |
|---|---|---|---|
| 2009/0041332 A1* | 2/2009 | Bhaskar | G01N 21/93 382/145 |
| 2009/0061543 A1* | 3/2009 | Ukraintsev | G01B 21/042 438/14 |
| 2012/0147363 A1 | 6/2012 | Suzuki et al. | |

FOREIGN PATENT DOCUMENTS

| | | |
|---|---|---|
| JP | 2011-75431 A | 4/2011 |
| JP | 2012-154820 A | 8/2012 |

OTHER PUBLICATIONS

Japanese-language Written Opinion (PCT/ISA/237) issued in PCT Application No. PCT/JP2014/081015 dated Jan. 13, 2015 (four (4) pages).

* cited by examiner

[FIG. 1]
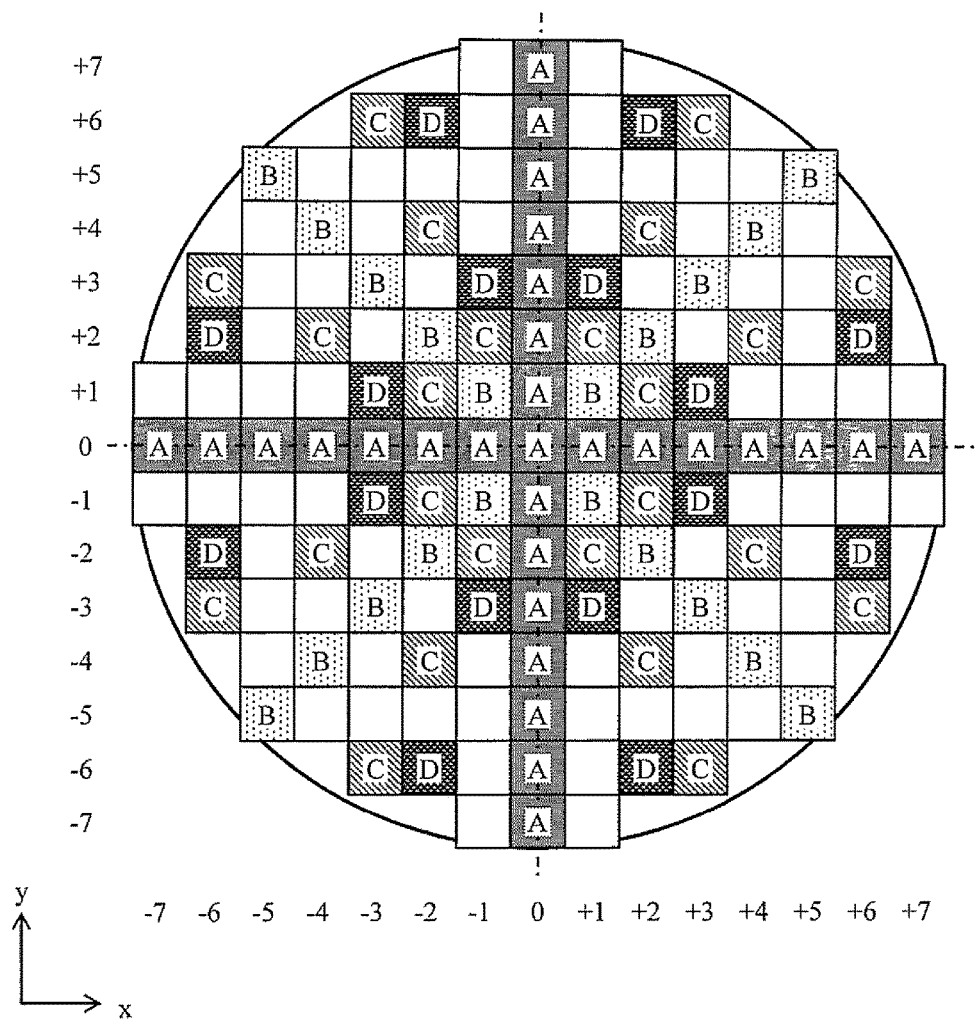
(RELATED ART EXAMPLE)

[FIG. 2]
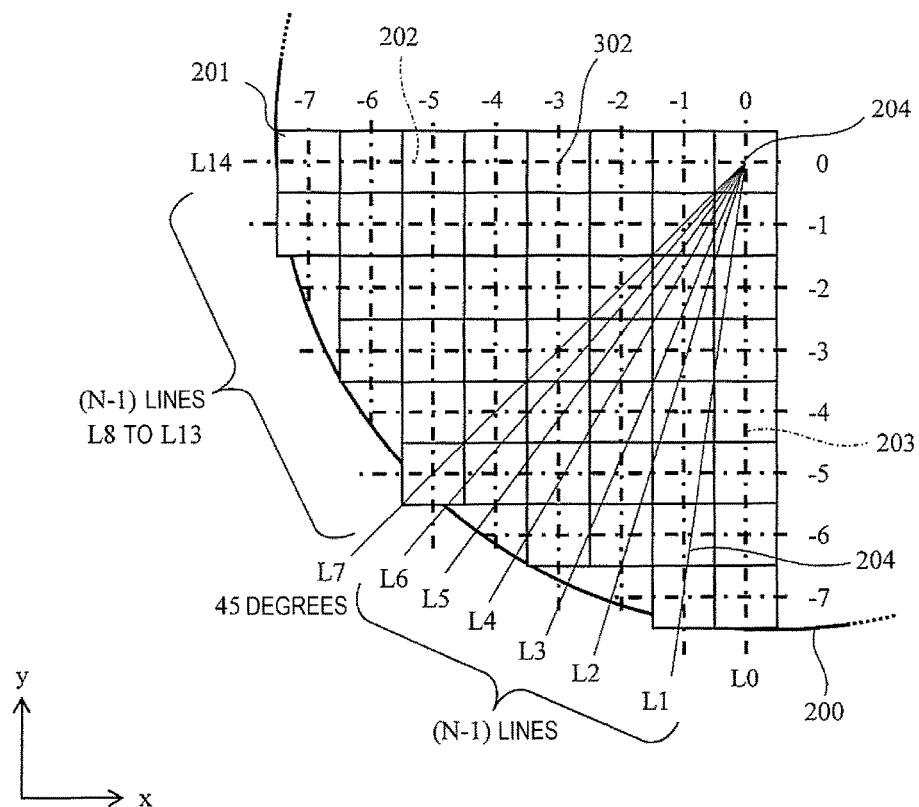

[FIG. 3]
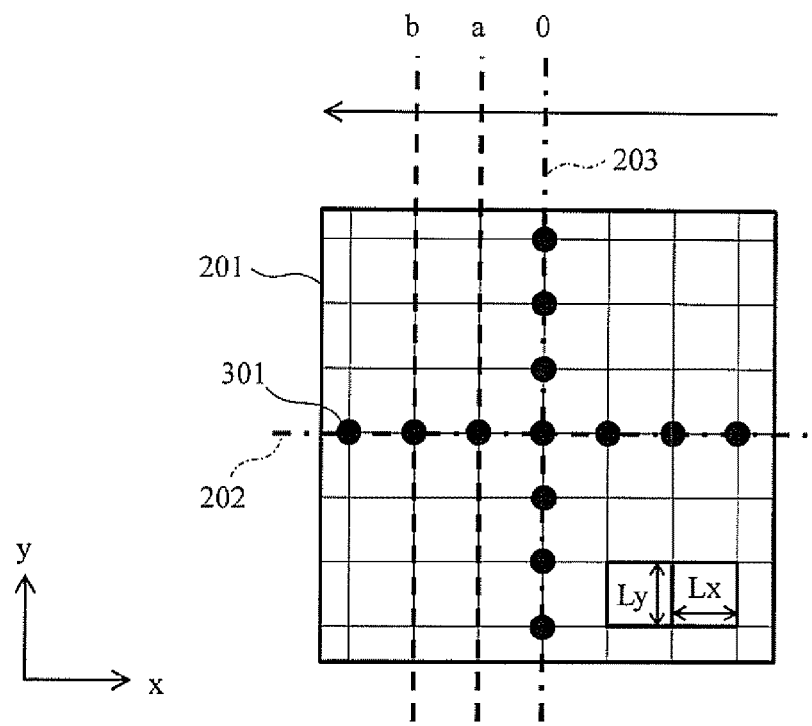
[FIG. 4]
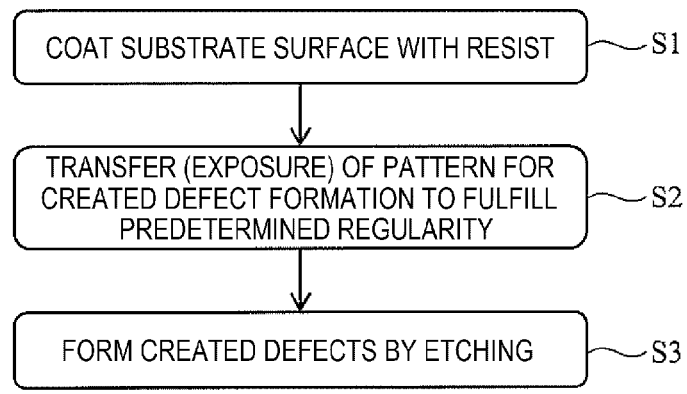

[FIG. 5]
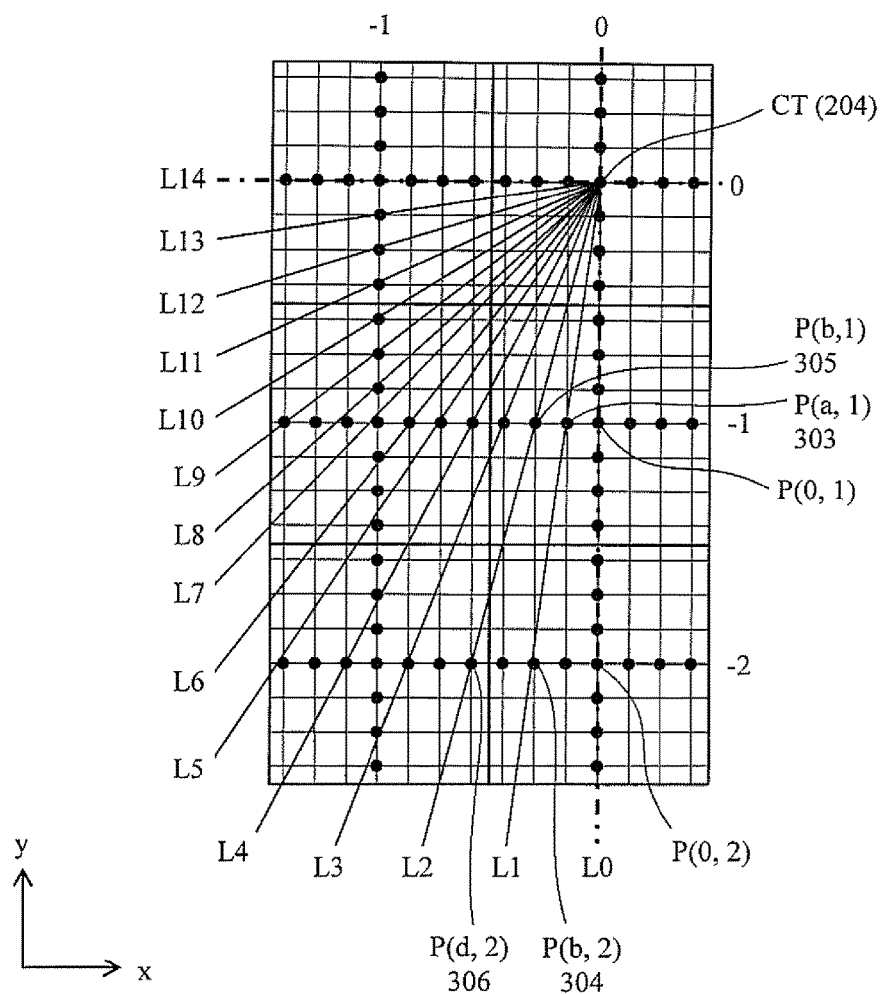

[FIG. 6]
| | CIRCULAR CYLINDER PROJECTION | SEMI-SPHERICAL PROJECTION | CIRCULAR CYLINDER HOLLOW | SEMI-SPHERICAL HOLLOW |
|---|---|---|---|---|
| TOP FACE SHAPE | | | | |
| SECTION SHAPE | | | | |
[FIG. 7]
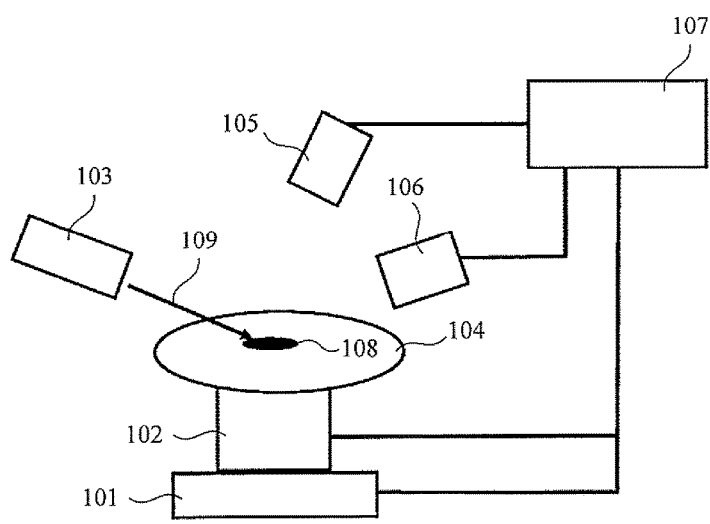

[Fig. 8A]
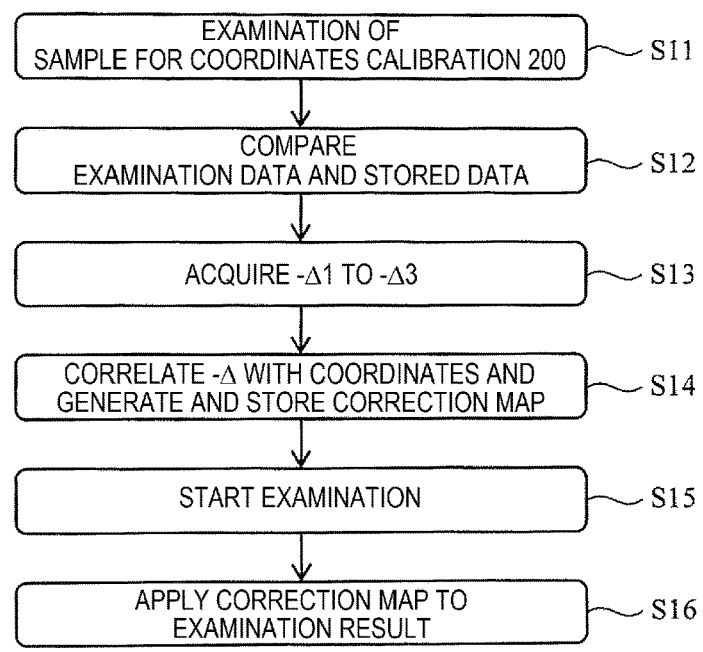
[Fig. 8B]
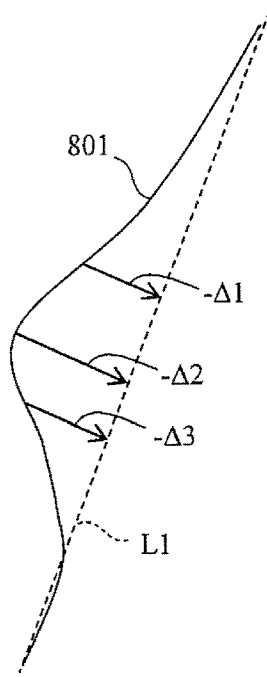

SAMPLE FOR COORDINATES CALIBRATION AND METHOD FOR FABRICATING THE SAME

TECHNICAL FIELD

This invention relates to a sample for coordinates calibration used in a surface inspection apparatus that examines defects on the sample and a method for fabricating the same.

BACKGROUND ART

In a semiconductor manufacturing process, defects including particles, scratches, etc. in a semiconductor substrate (wafer) surface cause failures including insulation failures, short circuit, etc. of wires formed on the wafer and cause insulation failure of capacitors and breakdown of gate oxide films. Accordingly, it is important to detect defects in the wafer surface in the semiconductor manufacturing process and feed back the defects to the semiconductor manufacturing process.

For the detection of defects, the so-called surface inspection apparatus is used. An example of the surface inspection apparatus includes an optical inspection apparatus that detects defects on a substrate by irradiating the substrate with examination light and detecting the scattered light. The optical inspection apparatuses may be roughly classified into surface inspection apparatuses that examine mirror wafers (bare wafers) and patterned wafer surface inspection apparatuses that examine wafers on which circuit patterns have been formed. In the specification, both inspection apparatuses are referred to as "surface inspection apparatuses" and their inspections are referred to as "surface inspections".

In a manufacturing process of a semiconductor device, a step of creating a resist pattern by transferring a pattern to a resist coating a wafer surface, a step of etching using the created resist pattern as a mask, and a step of removing unnecessary parts on the wafer surface are executed. Accordingly, particles, scratches, etc. attached to the wafer surface are a major factor for decline of yield.

On this account, in the respective manufacturing steps, the above described surface inspection apparatus is used for detection and management of particles attached to the wafer surface, defects existing on the wafer surface, etc. with high sensitivity and high throughput. Further, in the surface examination, wafer surface roughness has not only an influence on the performance of the photolithography process but also a significant influence on the detection sensitivity.

Accordingly, measurement of the wafer surface roughness is highly required.

CITATION LIST

Patent Literature

PTL 1: JP-A-2012-154820

SUMMARY OF INVENTION

Technical Problems

Now, for improvement and maintenance of yield of the manufacturing process, it is necessary to specify causes of defects and high power inspections are required. In the inspection, a surface inspection apparatus may be used. The surface inspection apparatus receives positions of defects from the surface inspection apparatus, and then, inspects the wafer surface with higher power than that of the surface inspection apparatus using charged particle radiation or the like. The coordinate accuracy of the surface inspection apparatus is generally higher than that of the surface inspection apparatus. Accordingly, in order for the surface inspection apparatus to quickly find defects, the higher coordinate accuracy than that of the surface inspection apparatus is required. That is, it is necessary that the coordinate accuracy of the surface inspection apparatus has been correctly calibrated in advance.

For the calibration of defect coordinates accuracy of the surface inspection apparatus, a wafer on which calibration points are laid out (sample for coordinates calibration) is used. FIG. 1 shows a related art example of the sample for coordinates calibration. In the sample for coordinates calibration used in related art, a virtual grid pattern in which unit grids (virtual chips) are respectively laid out at equal spaces in the x-axis direction and the y-axis direction is set on the surface of a wafer, and concave defects (artificial defects) are created at the center points of the unit grids forming the virtual grid pattern. The individual artificial defects correspond to the individual calibration points. FIG. 1 shows an image of the virtual grid pattern and a position relationship among the unit grids at equal spaces in the radial directions.

A surface inspection apparatus that manages coordinates in an r-theta coordinate system examines the entire surface of a wafer by moving a stage in the radial direction while rotating the wafer, and thereby, spirally moving an examination field on the wafer surface. In the specification, the examination system with the simultaneous rotation and linear movement of the wafer is also referred to as "R-θ system". In the case of the R-θ system, the track of the examination field is substantially spiral or concentric. Accordingly, in the surface inspection apparatus using the R-θ system, it is necessary to acquire error information of the coordinates given by R (position in radial direction) and θ (position in rotation direction) over the entire surface of the wafer before the start of the examination.

However, as described above, when the artificial defects are created only at the respective center points of the unit grids forming the grid pattern, the positions of the unit grids (virtual chips) containing the artificial defects appearing at equal spaces radially from the center point of the wafer are limited to positions of "A", "B", "C", "D" in FIG. 1. Accordingly, it is impossible to uniformly acquire the coordinates correction information (information for correcting error information) specific to the surface inspection apparatus within the wafer.

That is, since the distribution of the calibration points that provide coordinates correction information within the wafer surface is non-uniform (has sparse and dense parts), it is difficult to fully acquire error information of coordinates randomly existing within the wafer surface depending on the coordinates calibration sample used in related art (FIG. 1). Accordingly, in the surface inspection apparatus of related art, with respect to the area with sparse error information, the error information is generated by interpolation of the error information in the surrounding areas. However, the inventor has found that this causes variations in correction results and does not fulfill the required accuracy.

Solution to Problems

In order to solve the problems, the specification proposes a sample for coordinates calibration in which intentional defects are laid out at substantially uniform spaces with respect to radial and circumferential directions for providing reference points (calibration points) for defect coordinates calibration. The sample for coordinates calibration as one of representative inventions has "a substrate having a circular plate-shape, and multiple intentional defects that form a grid pattern with squares as unit grids on a surface of the substrate, the intentional defect providing a center point of the grid pattern coinciding with a center point of the substrate and, letting the maximum value of a number of the unit grids arranged from the center point of the substrate in radial directions be N (a natural number equal to or larger than two), a number of the intentional defects formed at equal spaces along one side of the unit grid being N+1 including the two intentional defects providing a vertex of the unit grid".

Further, a method for fabricating a sample for coordinates calibration as one of the representative inventions has "the steps of coating a surface of a substrate having a circular plate-shape with a resist, sequentially transferring unit exposure patterns on a surface of the resist by multiple exposure steps, letting the maximum value of a number of the unit exposure patterns arranged in radial directions including the unit exposure pattern used for formation of a center point of a grid pattern to be formed on the surface of the resist be M (a natural number equal to or larger than two), the unit exposure pattern having M−1 defect patterns forming a first grid line and M−1 defect patterns forming a second grid line that intersects with the first grid line in a cross form, and the defect pattern in common with the first and second grid lines providing a center of the unit exposure pattern and a space between two defect patterns adjacent on each grid line given by 1/(M−1)th of one side of the exposure pattern, and forming multiple intentional defects in the surface of the substrate by etching the surface of the substrate using a pattern formed using the exposed resist as a mask".

Advantageous Effects of Invention

According to the invention, the sample for coordinates calibration in which the intentional defects are laid out to provide reference points (calibration points) for defect coordinates calibration at substantially uniform spaces with respect to respective radial and circumferential directions can be realized. As a result, coordinates accuracy of the surface inspection apparatus may be remarkably improved as compared with related art. The other problems, configurations, and effects than those described above will be clear from the following explanation of the embodiment.

BRIEF DESCRIPTION OF DRAWINGS

FIG. 1 is a diagram for explanation of a coordinates calibration sample of related art.

FIG. 2 is a layout plan for explanation of a part (quarter) of a sample for coordinates calibration according to Example 1.

FIG. 3 is an enlarged view for explanation of a configuration of a unit exposure pattern.

FIG. 4 is a diagram for explanation of a manufacturing method of the sample for coordinates calibration according to Example 1.

FIG. 5 is a diagram for explanation of a position relationship (regularity) between intentional defects and a center point of the sample for coordinates calibration.

FIG. 6 is a diagram for explanation of shape examples preferably used for the intentional defects.

FIG. 7 is a diagram for explanation of a surface inspection apparatus.

FIGS. 8A and 8B are flowcharts for explanation of a coordinates calibration procedure in the surface inspection apparatus.

DESCRIPTION OF EMBODIMENT

As below, an embodiment of the invention will be explained with reference to the drawings. The embodiment of the invention is not limited to examples to be described later, but various modifications can be made within the technical scope thereof.

Example 1

FIG. 2 shows apart of a sample for coordinates calibration 200 according to the example. FIG. 2 shows only the third quadrant part of the sample for coordinates calibration 200 in which intentional defects are formed in a nearly circular plate-like substrate (having the same shape as a wafer). Note that the configurations of the sample for coordinates calibration 200 corresponding to the other quadrant parts are the same as that of the third quadrant. That is, in the respective quadrant parts, configurations formed by rotation of the configuration shown in FIG. 2 to 90°, 180°, 270° around the center point (0,0) of the sample for coordinates calibration 200 as a rotation center are provided.

In the specification, the sample for coordinates calibration 200 may be called a wafer for calibration or reference sample. The material of the substrate forming the sample for coordinates calibration 200 is e.g. silicon, sapphire, silica, or the like. As shown in FIG. 2, in the example, an arbitrary unit exposure area 201 is defined on the surface of the sample for coordinates calibration 200. The unit exposure area 201 may have substantially the same size as a chip (virtual chip). The unit exposure area 201 has e.g. a rectangle shape, more specifically, a square shape. Note that, in the specification, for convenience of explanation of regularity, the minimum unit of the exposure area is referred to as "unit exposure area", however, the unit exposure area may not have the same size as an area exposed to light at single exposure step. For example, multiple unit exposure areas may be exposed to light at single exposure step.

In the case of the example, the multiple unit exposure areas 201 are laid out on the surface of the substrate to form a grid pattern as the whole substrate. Accordingly, the unit exposure areas 201 are respectively laid out substantially in parallel with respect to an x-axis and a y-axis as a rectangular coordinate system (first rectangular coordinate system) of the substrate. In the case of FIG. 2, the coordinates of the unit exposure areas 201 may be expressed by "0" to "−7" with respect to the respective axis directions of the rectangular coordinate system (first rectangular coordinate system). For reference, the rectangular coordinate system (first rectangular coordinate system) is the same as that of the sample for coordinates calibration described in FIG. 1. The center of the sample for coordinates calibration 200 substantially coincides with the center of the virtual chip corresponding to (0,0) that provide the coordinate origin.

Hereinafter, it is assumed that the unit exposure area 201 has the same size as an area exposed to light at single exposure step. In the specification, a pattern to be exposed in the unit exposure area 201 is referred to as "unit exposure pattern". To the unit exposure pattern, multiple defect patterns 301 (FIG. 3) corresponding to the intentional defects, which will be described later, are assigned. The defect pattern 301 is an individual pattern like the intentional defect. In FIG. 2, virtual lines connecting the multiple defect patterns are shown by a line 202 and a line 203. The line 202 (lateral line) and the line 203 (longitudinal line) are straight lines passing through the center point of each unit exposure area 201 in parallel to the x-axis and the y-axis of a rectangular coordinate system (first rectangular coordinate system) of the substrate. As shown in FIG. 2, the line 202 (lateral line) and the line 203 (longitudinal line) divide the unit exposure area 201 into quarters. This means that the multiple defect patterns forming the line 202 (lateral line) and the line 203 (longitudinal line) are laid out to divide the unit exposure area 201 into quarters.

Under the regularity to be described later, when the intentional defects are formed in the substrate surface, virtual slant lines L1 to L13 slanting at respective predetermined angles with respect to the x-axis and the y-axis passing through the coordinate origin (0,0) may be defined on the substrate surface. Here, the coordinate origin (0,0) coincides with an intersection position of the virtual line L0 and the virtual line L14. The slant lines L1 to L13 respectively correspond to the virtual lines passing through the intentional defects laid out at equal spaces from the coordinate origin (0,0) in radial directions. Of the slant lines L1 to L13, the slant line L7 is substantially at 45 degrees with respect to the x-axis and the y-axis.

As below, the regularity that enables settings of the virtual slant lines L1 to L13 will be explained. Here, the maximum value of the number of unit exposure areas 201 laid out from the coordinate origin (0,0) in radial directions is N (a natural number equal to or larger than two, not including the unit exposure area 201 providing the coordinate origin in the number). In this case, as shown in FIG. 2, respective N−1 slant lines may be defined on both sides of the slant line L7. Note that the maximum value of the number is obtained with respect to the directions of the virtual line L0 and the virtual line L14.

FIG. 3 shows an enlarged view of the unit exposure pattern corresponding to the unit exposure area 201. FIG. 3 also shows the case where the unit exposure area 201 has the same size as the area exposed to light at single exposure step. As described above, the unit exposure area 201 does not necessarily have the same size as the area exposed to light at single exposure step. For example, the area exposed to light at single exposure step may have a size of two unit exposure areas 201. Also, in this case, the unit exposure pattern corresponding to one unit exposure area 201 is unchanged.

In the unit exposure pattern, the defect patterns 301 corresponding to the multiple intentional defects are formed. In the sample for coordinates calibration 200 in the example, the maximum value M of the number of unit exposure areas 201 laid out from the coordinate origin (0,0) in radial directions is eight including the unit exposure area 201 used for formation of the coordinate origin (0,0), and the numbers of defect patterns 301 are respectively provided as seven with respect to the x-axis direction and the y-axis direction. The relationship between the numbers is important. Note that, in the case of FIG. 2, the maximum value of the number is obtained with respect to the directions of the virtual line L0 and the virtual line L14.

Here, of the respective seven defect patterns 301 corresponding to the x-axis direction and the y-axis direction, one defect pattern 301 located at the center coincides with the center point of the unit exposure area 201 (i.e., the center point of the unit exposure pattern). Further, distances Lx and Ly of the adjacent two intentional defects 301 are substantially equal to 1/7th of one side of the unit exposure area 201. In other words, the distances Lx and Ly are equal to 1/(M−1)th of one side of the unit exposure pattern.

FIG. 4 shows a manufacturing method of the sample for coordinates calibration 200 according to the example.

(Step S1)

A semiconductor manufacturing apparatus (not shown) coats a surface of a substrate having nearly a circular plate-shape with a resist. For coating of the resist agent, a known semiconductor manufacturing apparatus is used.

(Step S2)

Then, the semiconductor manufacturing apparatus (e.g. exposure apparatus) repeatedly performs transfer (exposure) of a unit exposure pattern that fulfills predetermined regularity on a resist surface using an exposure optical system. The unit exposure pattern transferred by single exposure is formed by the multiple defect patterns 301 laid out crosswise as shown in FIG. 3. Here, the number of defect patterns 301 that provide two grid lines crossing in across form within the unit exposure pattern is M−1 (M is a natural number equal to or larger than two) per grid line. Further, the defect pattern 301 located at the intersection of the two grid lines coincides with the center point of the unit exposure pattern.

As described above, M is the maximum value of the number of unit exposure patterns (or unit exposure areas 201) arranged in the radial directions including the unit exposure pattern used for formation of the center point of the grid pattern to be finally formed on the substrate surface. The semiconductor manufacturing apparatus repeats the exposure step so that the unit exposure patterns (unit exposure areas 201) may be laid out on the entire surface of the substrate to form the grid pattern. Note that, as shown in FIG. 2, the layout of the unit exposure patterns is determined so that the center point of the substrate may coincide with the center point of the unit exposure pattern (i.e., the transfer position of the defect pattern 301).

(Step S3)

When the exposure ends, the semiconductor manufacturing apparatus (e.g. etching apparatus) etches the substrate surface using the resist pattern formed using the exposed resist as a mask, and forms multiple intentional defects in the surface of the substrate.

Here, the explanation of the regularity required for the unit exposure areas 201 used for manufacturing the sample for coordinates calibration 200 in which the intentional defects appear at equal spaces from the coordinate origin (0,0) in radial directions ends. Subsequently, regularity required for the intentional defects formed in the surface of the sample for coordinates calibration 200 will be explained.

As below, the coordinates of the intentional defects formed in the surface of the sample for coordinates calibration 200 will be explained in combination with coordinates information of the second rectangular coordinate system defined with respect to the substrate and coordinates information of the local first rectangular coordinate system defined with respect to the unit exposure area 201. For example, the position of the unit grid on the substrate is expressed by the coordinates information of the second rectangular coordinate system and the position of the intentional defect within the unit grid is expressed by the coordinates information of the first rectangular coordinate system. In the example of FIG. 3, "0", "a", "b", ... representing the coordinate positions in the x-direction within one unit exposure area 201 are used. The same applies to the y-axis direction. The positions of the individual intentional defects may be specified using the first and second rectangular coordinate systems.

Using FIG. 5, the regularity (position relationship) required between the intentional defects and the center 204 of the sample for coordinates calibration 200 will be explained. In the surface of the sample for coordinates calibration 200, the square unit grids are formed by the intentional defects shown by black circles in FIG. 5, and the grid pattern is formed by the collection of these unit grids. Note that the single unit grid is formed by four unit exposure patterns. As shown in FIG. 5, one of the intentional defects located at the intersection of the two grid lines and providing a vertex of the unit grid coincides with the center point of the sample for coordinates calibration 200 (substrate) (Rule 1). Here, letting the maximum value of the number of unit grids arranged from the center point of the sample for coordinates calibration 200 in the radial directions be N (a natural number equal to or larger than two), the number of intentional defects formed at equal spaces along one side of the unit grid is given by N+1 including the two intentional defects providing the vertex of the unit grid (Rule 2).

FIG. 5 shows an example with N of seven (see FIG. 2). Accordingly, on the respective sides forming the unit grid, eight intentional defects are laid out at equal spaces including the two intentional defects providing the vertex thereof. When attention is focused on the slant line L1, it is known from FIG. 5 that the distance from the center point 204 to the intentional defect 303 at the coordinates (a,1) and the distance from the intentional defect 303 at the coordinates (a,1) to the intentional defect 304 at the coordinates (b,2) are substantially equal. The distance is equal to the distance between the intentional defect 304 at the coordinates (b,2) and the intentional defect at the coordinates (c,3), the distance between the intentional defect at the coordinates (c,3) and the intentional defect at the coordinates (d,4), . . . . This means that all of the distances between the adjacent two intentional defects on the slant line L1 are equal.

Next, attention is focused on the slant line L2. It is known that the distance from the center point 204 to the intentional defect 305 at the coordinates (b,1) and the distance from the intentional defect 305 at the coordinates (b,1) to the intentional defect 306 at the coordinates (d,2) are substantially equal. The distance is equal to the distance between the intentional defect 306 at the coordinates (d,2) and the intentional defect at the coordinates (f,3) and the others. This means that all of the distances between the adjacent two intentional defects on the slant line L2 are equal.

With respect to the other slant lines L3, L4 . . . L13, all of the distances between the adjacent two intentional defects on the respective slant lines are equal. That is, letting the maximum value of the number of unit grids arranged from the center point of the sample for coordinates calibration 200 (substrate) in the radial directions be N (a natural number equal to or larger than two), the number of intentional defects formed at equal spaces along one side of the unit grid is determined as N+1 including the two intentional defects providing the vertex of the unit grid, and thereby, the distances between the adjacent two intentional defects on the same slant lines have constantly equal relationships. Accordingly, in the sample for coordinates calibration 200 of the example, the intentional defects appear at nearly uniform spaces with respect to the respective radial directions and circumferential directions.

Note that, in the case of the sample for coordinates calibration 200, the distance between the two intentional defects appearing in the same radial direction depends on the azimuth with respect to the coordinate origin (0,0) (depends on the orientation of the slant line), however, appearance frequencies of the intentional defects are uniform with respect to all azimuth directions. Accordingly, in the case where the sample for coordinates calibration 200 is used for the calibration of the coordinate system of the surface inspection apparatus that manages coordinates in the r-theta (R-θ) coordinate system (second rectangular coordinate system), more displacement information (error information) in the radial directions may be acquired than that for the sample for calibration of related art. Therefore, the accuracy of the coordinates correction information is remarkably improved. Consequently, the coordinates accuracy of the surface inspection apparatus may be improved more remarkably than that of related art.

Example 2

In the example, the method for fabricating the sample for coordinates calibration 200 is supplemented. The sample for coordinates calibration 200 may be fabricated by various methods. For example, as described above, the sample for coordinates calibration 200 may be fabricated by the so-called semiconductor process (including exposure and etching). Further, the sample for coordinates calibration 200 may be fabricated by FIB (Focused Ion Beam). However, it is desirable to employ the semiconductor process for the fabrication of the sample for coordinates calibration 200.

This is because the layout accuracy of the intentional defects fabricated by FIB depends on performance of an FIB apparatus. Further, regarding FIB, processable shapes and sizes are limited and processing uniformity has difficulty. For example, in FIB, the processable shape is limited to a concave shape. Furthermore, in FIB, times taken for processing of the individual intentional defects are longer and the manufacturing cost of the sample for coordinates calibration 200 may be higher.

On the other hand, the semiconductor process has none of these disadvantages. Note that, in the case where the sample for coordinates calibration 200 is fabricated using the semiconductor process, it is desired to determine the spaces between the intentional defects according to the specifications of the exposure master. Further, in the case where the sample for coordinates calibration 200 is fabricated using the semiconductor process, the degree of freedom of change of the spaces between the intentional defects may be made very high according to calibration target accuracy.

For example, at least one of the shape and the size of the intentional defect may be determined by the configuration of the surface inspection apparatus (at least one of a spatial layout and an aperture size of a detector). In the example, the specifications of the intentional defects are selected according to the configuration of the surface inspection apparatus. For example, the specifications are determined so that the multiple intentional defects may not be included within the same detection field of the surface inspection apparatus and within an area corresponding to resolution of the processing apparatus.

The intentional defects may be designed in consideration of an incident angle of an examination illumination of the surface inspection apparatus. For example, in the case where the rectangle or slit defects are detected, the optical diffraction angles of the intentional defects are considered.

In some circumstances, the sample for coordinates calibration 200 includes a material that is stable to the usage environment of the surface inspection apparatus (e.g. at least one of $SiO_2$ and SiN). The sample for coordinates calibration 200 desirably includes a material that is substantially stable or substantially has stiffness to the light having a predetermined wavelength. As a predetermined wavelength, e.g. an ultraviolet (UV) region, deep UV (DUV) region, and extreme UV (EUV) are considered. More specifically, a band from about 10 nm to 400 nm is considered.

Further, it is preferable to use a material by which sufficient scattering light intensity is obtained with respect to the illumination condition of the surface inspection apparatus for the intentional defects. Note that the reflection coefficient and the absorption coefficient for the illumination wavelength are considered. Furthermore, it is preferable that the intentional defect has a shape by which stable scattering light is obtained with respect to the illumination condition of the surface inspection apparatus. For example, the shape by which no interference occurs with respect to the illumination wavelength or the calibration is not hindered is desirable.

It is preferable that the intentional defect has a shape by which stable scattering light is obtained with respect to the illumination condition of the surface inspection apparatus. Note that stability to illumination energy or no damage thereby is considered. It is preferable that the intentional defect has a shape by which the same scattering light intensity is obtained regardless of the azimuth even when the illumination wavelength of the surface inspection apparatus changes. For example, it is preferable that a Rayleigh scattering phenomenon occurs at about ⅓rd of the illumination wavelength or less.

Example 3

FIG. 6 shows shape examples preferably used for the intentional defects. FIG. 6 shows a circular cylinder projection, a semi-spherical projection, a circular cylinder hollow, and a semi-spherical hollow as the shape examples preferably used for the intentional defects. Note that it is desirable that the shape and the dimensions of the intentional defect are smaller with respect to the illumination wavelength of the surface inspection apparatus, more specifically, sufficiently smaller and substantially the same in every direction. Therefore, it is preferable that the shape of the intentional defect is circular cylinder and semi-sphere as seen from above in the vertical direction, easily manufactured as the exposure process, and satisfies the above described requirement conditions.

Further, the shape of the intentional defect may be selected at a very high degree of freedom using a combination of the specifications of the exposure master and the exposure process. For example, a planar shape such as a rectangle (with a selectable aspect ratio) and a circle (sphere) may be selected or the size (area, height, volume) can be selected.

Example 4

FIG. 7 shows the surface inspection apparatus that calibrates coordinates using the above described sample for coordinates calibration 200. A spindle 102 is a mechanism of rotating the mounted sample for coordinates calibration 200 at a coordinates calibration and rotating a mounted wafer 104 at an examination. As below, the wafer 104 will be explained. An XY stage 101 is a mechanism of linearly moving the spindle 102 in the radial direction of the wafer 104 while the wafer 104 rotates.

An illumination optical system 103 includes a light source and optical elements. The optical elements include a mirror and a lens. The illumination optical system. 103 irradiates the wafer 104 with light and forms an illuminated area 108 on the substrate surface. The track of the illuminated area 108 is substantially spiral or concentric. The R-θ system is realized by a combination of the spindle 102 and the stage 101.

A first detection optical system 105 includes a lens that collects light scattered from the wafer 104 and a detector that converts the scattering light into first data. The first detection optical system 105 may be formed by an imaging system including an imaging lens, a spatial filter, and an image sensor having multiple pixels. A second detection optical system 106 includes a lens that collects light scattered from the wafer 104 and a detector that converts the scattering light into second data. The second detection optical system 106 may be formed by an imaging system including an imaging lens, a spatial filter, and an image sensor having multiple pixels. The first detection optical system 105 and the second detection optical system 106 are laid out in spatially different positions.

The first data and the second data are transmitted to a processing system 107 and processed. The processing system 107 detects defects on the wafer 104 using at least one of the first data and the second data. The defect detection is performed by comparison between at least one of the first data, the second data, and data obtained by predetermined processing on the first and second data and a threshold value. For example, if there is data larger than the threshold value, the processing system 107 determines that the data is information from the defects. The processing system 107 stores the coordinates at which the data determined to be defects are obtained in a memory (not shown). The processing system 107 includes a display for presenting examination results to an operator.

FIG. 8 shows a flow of calibration processing executed by the processing system 107.

(Step S11)

Prior to the examination of the wafer 104, the surface inspection apparatus examines the sample for coordinates calibration 200.

(Step S12)

The processing system 107 compares examination data of the intentional defects detected with respect to the sample for coordinates calibration 200 and data on the sample for coordinates calibration 200 stored in advance. More specifically, the processing system 107 compares an approximate curve 801 with respect to the detected intentional defects and an arbitrary slant line (e.g. L1) stored in advance as described in FIG. 8(b). The processing system 107 obtains displacement Δ from the comparison result. The displacement corresponds to the above described error information.

(Step S13)

The processing system 107 calculates an amount of error correction (−Δ) that cancels the displacement Δ. The displacement Δ can vary depending on the coordinate position, and thus, the processing system 107 may obtain multiple amounts of error correction (−Δ) (e.g. −Δ1, −Δ2, −Δ3) (see FIG. 8(b)).

(Step S14)

The processing system 107 creates a correction map by correlation of the obtained amounts of error correction (−Δ) with coordinates, and stores the created correction map in the memory. Here, calibration processing of coordinates errors specific to the drive mechanism of the surface inspection apparatus (coordinates calibration processing) ends.

(Step S15)

Then, the examination of the wafer 104 is started. The wafer 104 is an arbitrary examination sample.

(Step S16)

The processing system 107 drive-controls the spindle 102 and the stage 101 so that the examination area may be located in the coordinate position corrected using the previously created correction map.

Note that the sample for coordinates calibration 200 may be incorporated into the surface inspection apparatus. In this case, the sample for coordinates calibration 200 is substantially an element of the surface inspection apparatus.

Other Examples

The invention is not limited to the above described examples, but includes various modified examples. For example, the above described examples are explained in detail for clear explanation of the invention, and not all of the explained configurations are necessarily provided. Further, a part of a certain example may be replaced by a configuration of another example. Furthermore, a configuration of a certain example may be added to a configuration of another example. Moreover, with respect to part of the configurations of the respective examples, part of configurations of another example may be added, deleted, or replaced.

Part of all of the above described respective configurations, functions, processing units, processing means, etc. may be realized by hardware by design using integrated circuits or the like, for example. Further, the above described respective configurations, functions, etc. may be realized by interpretation and execution of programs for realization of the respective functions by a processor (as software). Information of programs, tables, files, etc. for realization of the respective functions may be stored in a memory device including a memory, hard disc, SSD (Solid State Drive) or a memory medium including an IC card, SD card, DVD. Furthermore, control lines and information lines considered as being necessary for explanation are shown and not all of the control lines and information lines necessary for products are shown. In practice, it may be considered that almost all of the configurations are mutually connected.

REFERENCE SIGNS LIST

101 . . . XY stage
102 . . . spindle
103 . . . illumination optical system
104 . . . wafer
105 . . . first detection optical system
106 . . . second detection optical system
107 . . . processing system
108 . . . illuminated area
200 . . . sample for coordinates calibration
201 . . . unit exposure area
204 . . . center point
301 . . . defect pattern
303, 304, 305, 306 . . . intentional defects

The invention claimed is:

1. A wafer for coordinates calibration comprising:
multiple unit exposure areas having multiple intentional defects that form a grid pattern with squares as unit grids on a surface of the wafer, the multiple intentional defects providing a center point of the grid pattern coinciding with a center point of the wafer,
wherein, when a maximum value of a number of the multiple unit exposure areas arranged from a coordinate origin in a radial direction is M (a natural number equal to or larger than two), the number of intentional defects in the multiple unit exposure areas forming each of two respective grid lines that intersect in a cross form and including the center point is M−1, and a distance between two adjacent intentional defects is 1/(M−1).

2. The wafer for coordinates calibration according to claim 1, wherein the wafer for coordinates calibration is used for a coordinates calibration of a surface inspection apparatus that manages coordinates of the wafer in an r-theta coordinate system.

3. The wafer for coordinates calibration according to claim 1, wherein the intentional defect is formed by a material having stiffness to light in a wavelength band in an ultraviolet region, deep ultraviolet region and/or extreme ultraviolet region.

4. The wafer for coordinates calibration according to claim 1, wherein the intentional defect has a projection shape.

5. The wafer for coordinates calibration according to claim 1, wherein the intentional defect has a circular cylinder shape or semi-spherical shape.

6. The wafer for coordinates calibration according to claim 1, wherein the intentional defect is fabricated by a semiconductor process including exposure and etching.

7. The wafer for coordinates calibration according to claim 1,
wherein, when a maximum value of a number of the unit grids arranged from the center point of the substrate in radial directions is N (a natural number equal to or larger than two), a number of the intentional defects formed at equal spaces along one side of the unit grid is N+1 including two intentional defects providing a vertex of the unit grid.

8. A method for fabricating a sample for coordinates calibration comprising the steps of:
coating a surface of a substrate having a circular plate-shape with a resist;
sequentially transferring unit exposure patterns on a surface of the resist by multiple exposure steps, letting a maximum value of a number of the unit exposure patterns arranged in radial directions including the unit exposure pattern used for formation of a center point of a grid pattern to be formed on the surface of the resist is M (a natural number equal to or larger than two), the unit exposure pattern having M−1 defect patterns forming a first grid line and M−1 defect patterns forming a second grid line that intersects with the first grid line in a cross form, and the defect pattern in common with the first and second grid lines providing a center of the unit exposure pattern and a space between two defect patterns adjacent on each grid line given by 1/(M−1)th of one side of the exposure pattern; and
forming multiple intentional defects in the surface of the substrate by etching the surface of the substrate using a pattern formed using the exposed resist as a mask.

9. The method for fabricating the sample for coordinates calibration according to claim 8, wherein the multiple intentional defects are for formation of a grid pattern with squares as unit grids on a surface of the substrate and the intentional defect providing the center of the grid pattern coincides with a center point of the substrate, and, letting the maximum value of a number of the unit grids laid out from the center point of the substrate in radial directions be N (a natural number), a number of the intentional defects formed at equal spaces along one side of the unit grid is N+1 including the two intentional defects providing a vertex of the unit grid.

10. The method for fabricating the sample for coordinates calibration according to claim 8, wherein the intentional defect is formed by a material having stiffness to light in a wavelength band in an ultraviolet region, deep ultraviolet region and/or extreme ultraviolet region.

11. The method for fabricating the sample for coordinates calibration according to claim 8, wherein the intentional defect has a projection shape.

12. The method for fabricating the sample for coordinates calibration according to claim 8, wherein the intentional defect has a circular cylinder shape or semi-spherical shape.

* * * * *